(12) United States Patent
Beger et al.

(10) Patent No.: US 9,314,281 B2
(45) Date of Patent: Apr. 19, 2016

(54) ORTHOPAEDIC FIXATION SYSTEM, TARGETING DEVICE FOR SUCH A FIXATION SYSTEM AND ORTHOPAEDIC FIXATION METHOD

(71) Applicant: Aesculap AG, Tuttlingen (DE)

(72) Inventors: Jens Beger, Tuttlingen (DE); Josef Kozak, Tuttlingen (DE)

(73) Assignee: Aesculap AG (DE)

( * ) Notice: Subject to any disclaimer, the term of this patent is extended or adjusted under 35 U.S.C. 154(b) by 365 days.

(21) Appl. No.: 13/650,326

(22) Filed: Oct. 12, 2012

(65) Prior Publication Data

US 2013/0066387 A1    Mar. 14, 2013

Related U.S. Application Data

(63) Continuation of application No. PCT/EP2011/055172, filed on Apr. 4, 2011.

(30) Foreign Application Priority Data

Apr. 14, 2010  (DE) .......................... 10 2010 016 448

(51) Int. Cl.
*A61B 17/70*    (2006.01)
*A61B 17/17*    (2006.01)
(Continued)

(52) U.S. Cl.
CPC ......... *A61B 17/7083* (2013.01); *A61B 17/7092* (2013.01); *A61B 17/1703* (2013.01);
(Continued)

(58) Field of Classification Search
CPC .................................. A61B 17/7083–17/7089

USPC ......... 606/246–279, 86 A; 600/424, 437–472
See application file for complete search history.

(56) References Cited

U.S. PATENT DOCUMENTS 5,758,650 A * 6/1998 Miller et al. .................. 600/461
6,203,499 B1 * 3/2001 Imling et al. .................. 600/461
(Continued)

FOREIGN PATENT DOCUMENTS

DE    19921279 C1    11/2000
DE    10027988 A1    10/2002
(Continued)

OTHER PUBLICATIONS

International Application Serial No. PCT/EP2011/055172, International Search Report mailed Jul. 6, 2011, 5 pgs.
(Continued)

*Primary Examiner* — Todd E Manahan
*Assistant Examiner* — Michelle C Eckman
(74) *Attorney, Agent, or Firm* — RatnerPrestia

(57) ABSTRACT

An orthopaedic fixation system includes an anchoring element, which can be anchored to a bone and can be connected to a further anchoring element by means of a stabilization element. The anchoring element may include a stabilization element seating, into which the stabilization element can be guided. The orthopaedic fixation system may also include an extension device for the anchoring element having a longitudinal extent with a proximal section and a distal section. The distal section can be detachably fixed to the anchoring element. The fixation system may further include a holding device with a probe seating for an extracorporeal ultrasound probe and a coupling device for coupling the holding device to the proximal section of the extension device. A targeting device for a fixation system and an orthopaedic fixation method are also described.

21 Claims, 9 Drawing Sheets

(51) Int. Cl.
*A61B 17/86* (2006.01)
*A61B 19/00* (2006.01)
*A61B 17/34* (2006.01)

(52) U.S. Cl.
CPC ............ *A61B17/8605* (2013.01); *A61B 19/26* (2013.01); *A61B 2017/3413* (2013.01); *A61B 2019/267* (2013.01); *A61B 2019/5276* (2013.01)

(56) References Cited

U.S. PATENT DOCUMENTS

| | | | |
|---|---|---|---|
| 6,226,548 B1 * | 5/2001 | Foley ................ | A61B 17/7083 600/426 |
| 6,485,426 B2 * | 11/2002 | Sandhu ........................ | 600/461 |
| 6,695,781 B2 * | 2/2004 | Rabiner et al. ................ | 600/439 |
| 6,719,692 B2 | 4/2004 | Kleffner | |
| 6,796,988 B2 * | 9/2004 | Melkent et al. ............... | 606/130 |
| 6,849,047 B2 | 2/2005 | Goodwin | |
| 6,908,433 B1 * | 6/2005 | Pruter ........................... | 600/459 |
| 6,980,849 B2 * | 12/2005 | Sasso ............................ | 600/426 |
| 6,993,374 B2 * | 1/2006 | Sasso ............................ | 600/426 |
| 7,022,082 B2 * | 4/2006 | Sonek ........................... | 600/461 |
| 7,107,091 B2 * | 9/2006 | Jutras et al. ................... | 600/429 |
| 7,455,685 B2 | 11/2008 | Justis | |
| 7,473,267 B2 | 1/2009 | Nguyen | |
| 7,520,879 B2 * | 4/2009 | Justis et al. ................. | 606/86 A |
| 7,635,336 B1 * | 12/2009 | Pruter ........................... | 600/461 |
| 7,691,066 B2 * | 4/2010 | Kosaku ......................... | 600/461 |
| 7,749,232 B2 * | 7/2010 | Salerni ......................... | 606/103 |
| 7,835,778 B2 * | 11/2010 | Foley et al. ................... | 600/407 |
| 7,840,256 B2 * | 11/2010 | Lakin et al. ................... | 600/426 |
| 7,846,103 B2 * | 12/2010 | Cannon et al. ................ | 600/439 |
| 7,926,776 B2 * | 4/2011 | Cermak ..................... | 248/311.2 |
| 7,959,573 B2 * | 6/2011 | Furia ............................. | 600/461 |
| 7,976,469 B2 * | 7/2011 | Bonde et al. ................. | 600/461 |
| 7,976,546 B2 * | 7/2011 | Geist et al. .................. | 606/86 A |
| 7,998,144 B2 * | 8/2011 | Schumacher et al. .......... | 606/99 |
| 8,070,751 B2 * | 12/2011 | Justis et al. ................. | 606/86 A |
| 8,092,458 B2 * | 1/2012 | Geist et al. .................. | 606/86 A |
| 8,092,460 B2 * | 1/2012 | Geist et al. .................. | 606/86 A |
| 8,092,461 B2 * | 1/2012 | Geist et al. .................. | 606/86 A |
| 8,092,495 B2 * | 1/2012 | Boulis et al. ................. | 606/246 |
| 8,100,951 B2 * | 1/2012 | Justis et al. ................. | 606/279 |
| 8,137,281 B2 * | 3/2012 | Huang et al. ................. | 600/461 |
| RE43,328 E * | 4/2012 | Foley et al. ................... | 600/424 |
| 8,180,429 B2 * | 5/2012 | Sasso ............................ | 600/424 |
| 8,235,998 B2 * | 8/2012 | Miller et al. ................ | 606/86 A |
| 8,239,001 B2 * | 8/2012 | Verard et al. ................. | 600/424 |
| 8,317,801 B2 * | 11/2012 | Geist et al. ....................... | 606/99 |
| 8,333,771 B2 * | 12/2012 | Geist et al. .................. | 606/86 A |
| 8,348,954 B2 * | 1/2013 | Carls et al. .................. | 606/86 A |
| 8,366,715 B2 * | 2/2013 | Geist et al. .................. | 606/86 A |
| 8,386,018 B2 * | 2/2013 | Stauch et al. ................. | 600/424 |
| 8,425,531 B2 * | 4/2013 | Salerni ......................... | 606/103 |
| 8,442,621 B2 * | 5/2013 | Gorek et al. .................. | 600/424 |
| 8,585,705 B2 * | 11/2013 | Richelsoph et al. ........ | 606/86 A |
| 8,706,185 B2 * | 4/2014 | Foley et al. ................... | 600/407 |
| 2002/0049377 A1 * | 4/2002 | Moctezuma De La Barrera et al. ............................. | 600/407 |
| 2002/0133079 A1 * | 9/2002 | Sandhu ........................ | 600/464 |
| 2002/0156376 A1 * | 10/2002 | Wang ..................... | A61B 8/0833 600/439 |
| 2005/0059885 A1 * | 3/2005 | Melkent et al. ............... | 600/424 |
| 2005/0059891 A1 * | 3/2005 | Kosaku ......................... | 600/439 |
| 2005/0065517 A1 * | 3/2005 | Chin .................. | A61B 17/3421 606/86 A |
| 2005/0080418 A1 * | 4/2005 | Simonson et al. .............. | 606/61 |
| 2005/0085714 A1 * | 4/2005 | Foley et al. ................... | 600/424 |
| 2005/0267373 A1 * | 12/2005 | Lee ............................... | 600/471 |
| 2006/0020211 A1 * | 1/2006 | Tokumoto et al. ............ | 600/464 |
| 2007/0162009 A1 * | 7/2007 | Chao et al. ..................... | 606/61 |
| 2007/0162010 A1 * | 7/2007 | Chao et al. ..................... | 606/61 |
| 2007/0198015 A1 * | 8/2007 | Foley et al. ..................... | 606/61 |
| 2007/0213714 A1 * | 9/2007 | Justis .................. | A61B 17/7002 606/86 A |
| 2008/0077139 A1 * | 3/2008 | Landry et al. ................... | 606/61 |
| 2008/0077155 A1 | 3/2008 | Diederich | |
| 2008/0146926 A1 | 6/2008 | Stauch | |
| 2008/0242989 A1 * | 10/2008 | Koide ........................... | 600/443 |
| 2009/0082666 A1 * | 3/2009 | Geist et al. .................... | 600/424 |
| 2009/0177083 A1 * | 7/2009 | Matsumura .................... | 600/437 |
| 2009/0228053 A1 | 9/2009 | Kolb | |
| 2009/0326586 A1 * | 12/2009 | Duarte .......................... | 606/264 |
| 2010/0041990 A1 * | 2/2010 | Schlitt et al. .................. | 600/439 |
| 2010/0069919 A1 | 3/2010 | Carls | |
| 2010/0222828 A1 * | 9/2010 | Stad et al. .................. | 606/86 A |
| 2010/0228303 A1 * | 9/2010 | Salerni ....................... | 606/86 A |
| 2010/0234725 A1 * | 9/2010 | Geist et al. .................... | 600/424 |
| 2011/0022088 A1 * | 1/2011 | Forton et al. .................. | 606/246 |
| 2011/0040340 A1 * | 2/2011 | Miller et al. ................ | 606/86 A |
| 2011/0184464 A1 * | 7/2011 | Fiorella ......................... | 606/264 |
| 2011/0201938 A1 * | 8/2011 | Hiki et al. ..................... | 600/461 |
| 2011/0238117 A1 * | 9/2011 | Geist et al. .................... | 606/263 |
| 2012/0179213 A1 * | 7/2012 | Geist et al. .................. | 606/86 A |
| 2012/0179214 A1 * | 7/2012 | Geist et al. .................. | 606/86 A |
| 2013/0096637 A1 * | 4/2013 | Richelsoph et al. ......... | 606/86 A |
| 2013/0268007 A1 * | 10/2013 | Rezach et al. ................. | 606/279 |
| 2014/0024945 A1 * | 1/2014 | Mung et al. ................... | 600/461 |
| 2014/0200445 A1 * | 7/2014 | Boezaart et al. .............. | 600/424 |

FOREIGN PATENT DOCUMENTS

| | | |
|---|---|---|
| DE | 102006059225 A1 | 6/2008 |
| EP | 0284055 A2 | 9/1988 |
| EP | 1997448 A1 | 12/2008 |
| WO | WO-2007146833 A2 | 12/2007 |

OTHER PUBLICATIONS

International Application Serial No. PCT/EP2011/055172, International Written Opinion mailed Jul. 6, 2011, 8 pgs.

* cited by examiner

ORTHOPAEDIC FIXATION SYSTEM, TARGETING DEVICE FOR SUCH A FIXATION SYSTEM AND ORTHOPAEDIC FIXATION METHOD

CROSS-REFERENCE TO RELATED APPLICATIONS

This application is a continuation under 35 U.S.C. §365 of international application number PCT/EP2011/055172, filed on Apr. 4, 2011, which claims priority to German application number 10 2010 016 448.8, filed Apr. 14, 2010. The contents of both applications are incorporated by reference herein in their entirety and for all purposes.

FIELD OF THE INVENTION

The present invention relates to an orthopaedic fixation system with an anchoring element, which is anchorable to a bone and is connectable to a further anchoring element by means of a stabilisation element, wherein the anchoring element comprises a stabilisation element seating, into which the stabilisation element is insertable, and also with an extension device for the anchoring element having a longitudinal extent as well as a proximal section and a distal section, which distal section is detachably fixable to the anchoring element.

In addition, the present invention relates to an ultrasonic targeting device for an orthopaedic fixation system.

In addition, the present invention relates to an orthopaedic fixation method, in which an orthopaedic fixation system, for example the aforementioned system, is used.

BACKGROUND OF THE INVENTION

Orthopaedic fixation systems serve to fix bones or bone fragments relative to one another. For example, the fixation system can be used in the area of spinal fixation, wherein anchoring elements in the form of bone screws are anchored on the vertebrae to be stabilised relative to one another. These are connected to one another by means of the stabilisation element in the form of a rod, which runs along the spinal cord and is secured by clamping into the stabilisation element seatings of the bone screws, i.e. the screw heads, for example.

Irrespective of where the fixation is used on the body, it is desirable to work in a minimally invasive manner. For example, percutaneous fixation methods have been developed, in which both the anchoring elements and the stabilisation element can be inserted into the body through only relatively small incisions. However, this makes alignment of the stabilisation element relative to the stabilisation element seating difficult, in particular when more than only two anchoring elements are to be connected to one another.

In order to align the stabilisation element correctly relative to an anchoring element to insert it into the stabilisation element seating in an insertion direction, it is known to pre-define a corresponding guide path for the stabilisation element. For example, in the case of fixation systems and fixation methods according to U.S. Pat. No. 7,455,685 B2 and DE 100 27 988 A1 extension devices are in each case detachably connected to the anchoring elements at a distal end. The respective proximal ends, i.e. the ends facing the operating surgeon, of the extension devices project out of the body and the stabilisation element is held on them to pivot along a circular arc. These fixation systems have the disadvantage that they are mechanically complex and the stabilisation element can only be guided through the anchoring elements along a circular arc.

Fixation systems and fixation methods are known from WO2007/146833 A2 and from U.S. Pat. No. 7,473,267 B2, in which extension devices are also detachably connected to the anchoring elements, and in which a guide element, e.g. a thin wire, is firstly threaded through the stabilisation element seatings before insertion of the stabilisation element. This likewise requires a high equipment expenditure as well as an additional work step.

There is a need to provide an orthopaedic fixation system and method that enable easier alignment of the anchoring element and the stabilisation element relative to one another and thus easier insertion of the stabilisation element into the stabilisation element seating.

SUMMARY OF THE INVENTION

In a first aspect of the invention, the orthopaedic fixation system comprises an anchoring element, which is anchorable to a bone and is connectable to a further anchoring element by means of a stabilisation element. The anchoring element comprises a stabilisation element seating, into which the stabilisation element is insertable, and also an extension device for the anchoring element. The extension device includes a longitudinal extent as well as a proximal section and a distal section, which distal section is detachably fixable to the anchoring element. The fixation system comprises a holding device with a probe seating for an extracorporeal ultrasound probe and also a coupling device for coupling the holding device to the proximal section of the extension device.

In a second aspect of the invention, a fixation method is provided. An orthopaedic fixation system is used with an anchoring element, which is anchored to a bone, which is connected by means of a stabilisation element to a further anchoring element. The stabilisation element is inserted into a stabilisation element seating of the anchoring element in an insertion direction. The fixation system includes an extension device for an anchoring element, which is detachably connected at a distal section to the anchoring element and projects out of the body at a proximal section. The proximal section of the extension device is coupled to a holding device for an extracorporeal ultrasound probe by means of a coupling device, and the ultrasound probe is positioned in a probe seating of the holding device and the stabilisation element is detected by means of the ultrasound probe.

BRIEF DESCRIPTION OF THE DRAWING FIGURES

The foregoing summary and the following description may be better understood in conjunction with the drawing figures, of which:

DETAILED DESCRIPTION OF PREFERRED EMBODIMENTS OF THE INVENTION

Figure 1:
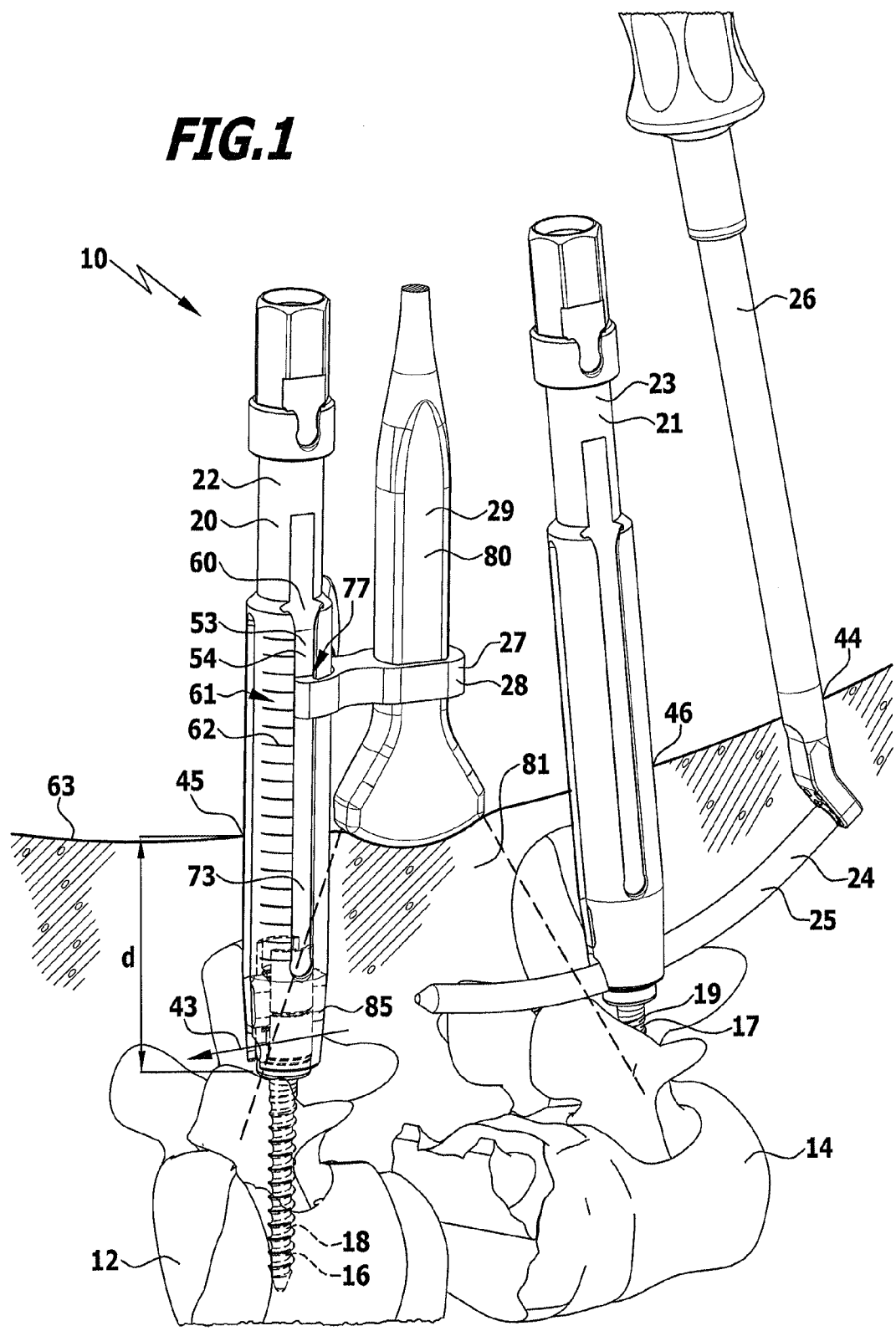
FIG. 1 is a perspective representation of a fixation system according to one aspect of the invention comprising, inter alia, a first holding device and an ultrasound probe, shown on application to a schematically represented vertebral column.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to an orthopaedic fixation system, comprising an anchoring element, which is anchorable to a bone and is connectable to a further anchoring element by means of a stabilisation element. The anchoring element comprises a stabilisation element seating, into which the stabilisation element is insertable, and also an extension device for the anchoring element. The extension device includes a longitudinal extent as well as a proximal section and a distal section, which distal section is detachably fixable to the anchoring element. The fixation system comprises a holding device with a probe seating for an extracorporeal ultrasound probe and also a coupling device for coupling the holding device to the proximal section of the extension device.

With the fixation system according to preferred embodiments of the invention in use the proximal section of the extension device projecting out of the body is coupled to the holding device by means of the coupling device. A probe seating for an ultrasound probe is arranged on the holding device. The ultrasound probe is secured detachably or non-detachably, for example, in the probe seating. The subcutaneously located operating area can be scanned in a user-friendly manner by means of the ultrasound probe and displayed in the ultrasound image using a display unit connected to the ultrasound probe. In particular, it is possible to detect and display both the stabilisation element seating and the stabilisation element. This gives the operating surgeon the ability to align the stabilisation element relative to the stabilisation element seating in a user-friendly manner and to insert it into said seating for instance in a defined insertion direction, because he/she can be guided by the ultrasound image. For alignment the operating surgeon can, for example, grasp the extension device and also the stabilisation element possibly by means of a tool secured to this. Because of the coupling of the holding device to the extension device, the ultrasound probe is in a defined spatial relationship to the stabilisation element seating. Thus, it is additionally possible in particular to detect a movement of the stabilisation element seating resulting from grasping the extension device directly by means of the ultrasound probe and display this in the ultrasound image. This makes the alignment of the stabilisation element and the stabilisation element seating relative to one another significantly easier for an operating surgeon.

The fixation system according to preferred embodiments of the invention is further distinguished by only a low equipment expenditure. Thus, already existing ultrasound probes can be used with the fixation system by using an appropriately adapted holding device and extension device. Furthermore, because no further incisions, apart from the incisions for the extension device and the stabilisation element, are necessary in the body, work can proceed in an especially minimally invasive manner.

Unless mentioned otherwise or evident from the context, the following statements are to be regarded as relating to use of the fixation system according to specification.

The stabilisation element seating preferably comprises an insertion opening, through which the stabilisation element is insertable into the stabilisation element seating in a defined insertion direction. As a result, it can be assured that the stabilisation element is aligned correctly relative to the stabilisation element seating before it is secured to this.

The holding device and the extension device can be coupled or are capable of being coupled mechanically to one another, for example, in a structurally simple manner. However, a different type of coupling is also possible, e.g. a magnetic coupling.

It is favourable if the holding device and the extension device are coupled rigidly to one another by means of the coupling device. The fixation system is thus given a particularly simple structural form.

For this, for example, the holding device and the extension device can be fixedly connected to one another by means of the coupling device and can thus be connected non-detachably and immovably to one another.

The fixation system is given a particularly simple structural form if the holding device and the extension device are connected to one another in one piece.

The holding device is preferably able to be detachably coupled to the extension device. This has the advantage that the holding device can be used with the fixation system only when it is actually required. For example, the extension device can also be a device that is usable for other purposes than coupling to the ultrasound probe, for instance a working cannula, a repositioning lever or the like. When the holding device is needed, it can be coupled to the extension device. When the holding device is no longer needed, it can be uncoupled from the extension device.

Advantageously, the holding device is transferable relative to the extension device from a first coupling position into a second coupling position and vice versa, wherein in the first coupling position and in the second coupling position the probe seating is arranged in particular on diametrically opposed sides of the extension device. Areas of the body arranged on opposite sides of the extension device can be detected in this way by means of the ultrasound probe in the first and in the second coupling position. This is of advantage in particular when the stabilisation element coming from a first anchoring element is guided through the stabilisation element seating of the (second) anchoring element, to which the extension device is connected, and is guided further in the direction of a third anchoring element. Thus, by means of the ultrasound probe the "coming" stabilisation element can be detected in the first coupling position and the "going" stabilisation element can be detected in the second coupling position. The fixation system is thus usable in a particularly versatile manner. If the fixation system is a spinal fixation system, a cranial-caudal region in relation to the extension device can firstly be viewed, for example, and then a caudal-cranial region. For example, in both coupling positions in the aforementioned insertion direction the probe seating is arranged on opposite sides of the extension device.

Overall, it is advantageous if the holding device and the extension device are configured to be movable relative to one another. This gives the possibility to flexibly adapt the fixation system to requirements predetermined by the respective use.

The holding device is preferably configured to be displaceable in axial direction relative to the extension device, i.e. along an axis defined by the extension device. The extension device having a longitudinal extent can define an axis, along which the holding device can be moved relative to the extension device, i.e. from proximal to distal and vice versa, for example. It is thus possible to likewise displace the ultrasound probe from proximal to distal and vice versa in order to apply the ultrasound probe reliably on the skin surface. As a result, the fixation system can be flexibly adapted to the requirements of the respective use.

It is advantageous if the holding device is configured to be lockably movable relative to the extension device. This makes working with the fixation system easier for the operating surgeon. The extension device and the holding device can be locked relative to one another when the operating surgeon has adjusted their relative position in accordance with the requirements predetermined by the use of the fixation system.

Advantageously, the fixation system comprises a fixation device for fixing the holding device relative to the extension device.

The holding device and the extension device can be fixed relative to one another in a particularly user-friendly manner if the fixation device is operable without any tool. It is particularly preferred if the fixation device can configured to be operable with only one hand.

Advantageously, the fixation device is configured as a clamping device. This allows the fixation system to be given a structurally simple form.

It has proved advantageous if the fixation device comprises a clamping screw for clamping the holding device relative to the extension device. The clamping screw can be screwed, for example, through a section of the holding device having a thread and be supported against the extension device, so that the holding device can be clamped in relation to the extension device. It can be configured in the form of a thumb screw or a tommy screw, for example, so that manual operation, and in particular one-handed operation, of the fixation device is possible for the operating surgeon.

In an embodiment of a different type of the fixation system according to preferred embodiments of the invention the fixation device is configured as a locking device. This also enables the holding device to be fixed relative to the extension device in a user-friendly manner.

The fixation system preferably comprises an indicating arrangement, by means of which the penetration depth of the extension device into the body is determinable. As a result, it can then be determined in a simple manner at what body depth the extension device and thus the stabilisation element seating is located. This provides the possibility of superimposing a target mark such as a cross hair for instance in the ultrasound image, for example with a suitable evaluation and display unit for the ultrasound signals. As a result, the operating surgeon can locate the stabilisation element seating in a simpler manner and aim the stabilisation element at it.

In addition, the indicating arrangement can serve to determine the relative position of the holding device and the extension device to one another.

In a structurally simple configuration the indicating arrangement comprises a scale arranged on the extension device. The scale can be located, for example, to be easily visible on the outside on the extension device and it can extend from the proximal section to the distal section.

The coupling device preferably comprises at least one first coupling member included or formed by the extension device and also at least one second coupling member, which is included or formed by the holding device and cooperates with the at least one first coupling member. The holding device and the extension device are coupled or able to be coupled by means of the coupling members. If the former are rigidly coupled and in particular connected to one another, as mentioned above, the first and second coupling members can be connected to one another and in particular be connected to one another in one piece.

It is advantageous if at least one coupling member is configured as a seating and the further coupling member cooperating with it is configured as a projection, as a result of which the fixation system can be provided with a simple structural form. For example, the at least one first coupling member of the extension device is configured as a seating and the at least one second coupling member of the holding device is configured as a projection. However, this could also be reversed.

The coupling members can be coupled to one another in a technically simple manner if the projection engages into the seating. A more reliable coupling is obtained if the projection engages in a positive-locking manner into the seating.

It is advantageous if the projection and the seating engage around or behind one another in a direction oriented transversely to an axis defined by the extension device. As a result, a reliable coupling of the holding device to the extension device can be assured and the holding device can be configured relative to the extension device in particular to be secured against rotation relative to the axis thereof. A particularly reliable coupling can be achieved if the projection and the seating engage around or behind one another in a positive-locking manner, as described above.

It is advantageous if the projection comprises a base region and a head region that widens relative to the base region and if the seating comprises a first seating region cooperating with the head region and a second seating region that is narrowed in relation to said first seating region and cooperates with the base region. As a result, it can be assured in a structurally simple manner that the projection and the seating engage around or behind one another as described above. The head region and the base region can merge continuously into one another, for example, as can the first seating region and the second seating region. In this way, the projection and the seating can form a dovetail-type connection and the holding device can thus be coupled to the extension device in a particularly reliable manner.

The seating preferably has an insertion opening for the projection, through which the projection is insertable into the projection and removable therefrom. The holding device can thus be attached to the extension device as required by inserting the projection through the insertion opening into the seating and thus coupling the holding device to the extension device. If the holding device is no longer needed, the projection can be removed from the seating and the holding device uncoupled from the extension device.

Advantageously, the seating is configured to widen in the region of the insertion opening. The widening of the seating makes insertion of the projection into the seating easier for the operating surgeon.

The insertion opening is preferably arranged on the seating at the end, since this also allows simple insertion of the projection into the seating as well as a simple structural configuration of the fixation system.

It is advantageous in particular if the insertion opening is arranged on a proximal end of the seating, since it can then be reached by an operating surgeon in a simpler manner. This makes coupling and uncoupling of the holding device and the extension device easier for the operating surgeon, in particular when the first coupling member of the extension device is a seating that has the insertion opening at the proximal end.

Advantageously, at least one coupling member has an extent in axial direction, i.e. along an axis defined by the extension device. The coupling member can thus form a guide element, for example, for the coupling member cooperating with it. A guidance of the holding device relative to the extension device can be assured as a result of this if these are configured to be movable and in particular displaceable relative to one another.

It can be specially provided that the coupling member having the axial extent is a seating, into which a coupling member in the form of a projection engages. The seating is then configured in particular in the form of an axially extending longitudinal groove, and the projection can form a slide block for instance that is displaceable along the seating.

It is advantageous if the at least one first coupling member is arranged on the extension device on the outside. An operating surgeon is thus given easy access to the coupling member, for instance to couple the holding device to the extension device or uncouple it therefrom.

Advantageously, two first coupling members are arranged on the extension device that are in particular diametrically opposed to one another in relation to the axis thereof. If the holding device has two second coupling members, this provides the possibility of coupling two respective coupling members to one another in pairs. As a result, a reliable coupling of the holding device and the extension device to one another can be assured. Moreover, there is the possibility of coupling the holding device to the extension device in the aforementioned first coupling position and second position. In the first coupling position the at least one second coupling member can cooperate with one of the first coupling members and in the second coupling position the at least one second coupling member can cooperate with the other of the first coupling members. This enables two regions of the body that are in particular diametrically opposed to one another to be detected by means of the ultrasound probe.

It is advantageous if two second coupling members are arranged on the holding device that are in particular diametrically opposed to one another in relation to an axis of the extension device. As in the previously described embodiment, each of the two second coupling members of the holding device can accordingly couple with the at least one first coupling member of the extension device.

To obtain a simple structure and a compact design it has proved to be expedient if the at least one second coupling member is arranged on the holding device at the end.

It has also proved to be expedient for a simple structural form and a compact design if the holding device comprises a coupling section, which includes or forms the at least one second coupling member, and a holding section connected to said coupling section, which includes or forms the probe seating.

The coupling section preferably has a contour adapted to an outer contour of the extension device. The contours adapted to one another can be recognised by an operating surgeon to make coupling of the holding device to the extension device easier. Moreover, there is the possibility that the coupling section and the extension device form cooperating guide elements when the holding device moves relative to the extension device.

The contour is preferably semicircular or substantially semicircular and the at least one coupling member is arranged on the coupling section on a side facing a centre of curvature of the contour. If the extension device has a cylindrical or substantially cylindrical cross-section, the coupling section is thus adapted to the outer contour of the extension device. The at least one second coupling member can cooperate with a first coupling member arranged on the extension device on the outside, e.g. engage radially into this or vice versa.

The probe seating preferably comprises a through opening for the ultrasound probe formed on the holding section. The holding device can be provided with a simple structural form as a result of this. The ultrasound probe, at a grip area for instance, can be passed through the through opening and held therein, for example by clamping.

However, it is also possible that the ultrasound probe is held in the probe seating in a different manner than by clamping.

In a particularly simple structural configuration of the holding device the through opening is configured as a perforation of the holding section.

It is advantageous if the probe seating includes or forms an enclosed edging for the through opening. If the size of the through opening is adapted to the size of a section of the ultrasound probe arranged in the through opening, e.g. of a grip area, a reliable hold and in particular clamping of the ultrasound probe in the probe seating can thus be assured. In particular, the edging can border the grip area of the ultrasound probe in a positive-locking manner.

It is advantageous if the through opening has a non-round cross-section. "Non-round" in the present case means that the through opening does not have a circular cross-section. The cross-section of the through opening can be, for example, elliptic, oval, rectangular (also with rounded corners) or in the form of a circle, from which two diametrically opposed segments have been separated. The non-round cross-sectional form of the through opening has the advantage that an operating surgeon is able to align the ultrasound probe correctly relative to the holding device, since ultrasound probes usually have a grip area with a cross-section that is not circular, i.e. non-round. If the cross-sectional form of the through opening is adapted to the cross-sectional form of the grip area and is non-round, the operating surgeon can insert the ultrasound probe into the probe seating in a clearly defined orientation. As a result, the ultrasound field emitted by the ultrasound probe enters into a clearly defined spatial relationship relative to the holding device and thus to the extension device and thus also to the anchoring element.

It is advantageous if the probe seating and in particular the through opening has its largest clear extent in a direction oriented parallel to the insertion direction in a plane that is spanned by the insertion direction and by an axis defined by the extension device. The usually non-round grip area of the ultrasound probe often has its largest cross-sectional extent in a plane, which is defined by the ultrasound field emitted by the ultrasound probe. Since the largest extent of the probe seating lies parallel to the insertion direction in the plane spanned by the insertion direction and by the axis of the extension device, this provides the possibility of emitting the ultrasound field in this plane referred to hereafter as "sagittal plane". The correct alignment of the stabilisation element relative to the stabilisation element seating can then be assured, for example, by checking in the ultrasound image that the stabilisation element is displayed lying in the sagittal plane which coincides with the plane of the ultrasound field.

It is still more advantageous if the probe seating, and in particular the through opening, has its largest clear extent in a plane that is spanned by the insertion direction and by an axis defined by the extension device. The ultrasound probe with the grip area, the largest cross-sectional extent of which lies in the sound field plane, can thus be inserted into the probe seating in only one way. This necessarily ensures emission of the ultrasound field in the sagittal plane.

The probe seating, and in particular the through opening, preferably has its largest clear extent in a direction perpendicular to a plane that is spanned by the insertion direction and by an axis defined by the extension device. An ultrasound probe with a grip area, the largest cross-sectional extent of which lies in a plane defined by the ultrasound field of the ultrasound probe, can then be inserted into the probe seating in such a manner that the sound field plane is oriented perpendicularly to the sagittal plane. The sound field plane is thus a plane referred to hereafter as "transversal plane". The operating surgeon can then recognise on the basis of the ultrasound image that the stabilisation element is aligned correctly relative to the stabilisation element seating when it intersects the sound field plane at as steep an angle as possible, ideally at right angles.

The three last-described advantageous embodiments of the fixation system can be formulated in general terms as follows:

It is advantageous if the ultrasound probe can be arranged in the probe seating in such a way that the ultrasound field emitted by the ultrasound probe lies in a plane that is spanned by the insertion direction and by an axis defined by the extension device (i.e. in the sagittal plane).

It is also advantageous if the ultrasound probe can be arranged in the probe seating in such a way that the ultrasound field lies in a plane that is oriented perpendicularly to the sagittal plane (i.e. in the transversal plane).

The coupling section and the holding section are preferably connected to one another in one piece, since this allows a simple structural form of the fixation system.

It is advantageous if the coupling section and the holding section are configured to be movable relative to one another. This provides the possibility of adapting the fixation system to the requirements arising as a result of its use in a more flexible manner.

Advantageously, the holding section is able to pivot relative to the coupling section around a pivot axis, which is oriented perpendicularly to a plane that is spanned by the insertion direction and by an axis defined by the extension device, i.e. perpendicularly to the sagittal plane. This provides the possibility of pivoting the ultrasound field in the insertion direction and against the insertion direction. This enables the stabilisation element to move towards the stabilisation element seating and to move away from this while constantly being detected by the ultrasound probe. This is achieved by pivoting the holding section relative to the coupling section. The insertion of the stabilisation element into the stabilisation element seating is thus even simpler for an operating surgeon.

The holding section and the coupling section preferably jointly form a hinge to pivot the holding section and the coupling section relative to one another in order to assure a simple structural form of the fixation system. The hinge can also be a film hinge.

It is advantageous if the holding section is configured to be linearly movable relative to the coupling section in a direction of movement that lies in a plane, which is spanned by the insertion direction and by an axis defined by the extension device, i.e. in the sagittal plane. In this way the holding section can be moved relative to the coupling section and thus relative to the extension device and to the stabilisation element seating in the insertion direction and opposite to the insertion direction. This provides the possibility of detecting the stabilisation element when it is moving towards and away from the stabilisation element seating by means of the ultrasound probe. This also makes alignment of the stabilisation element relative to the stabilisation element seating easier for the operating surgeon.

It is advantageous if the holding section and the coupling section jointly form a screw connection to move the holding section relative to the coupling section in order to configure the holding section to be linearly movable relative to the coupling section in a simple structural manner.

In a simple structural configuration of the fixation system the holding device is configured to be planar or substantially planar.

Advantageously, the holding device is configured to be intrinsically symmetrical in relation to a plane of symmetry, which is spanned by the insertion direction and by an axis defined by the extension device, i.e. the sagittal plane. The symmetrical configuration of the holding device allows its simple construction and simplifies its handling for the operating surgeon.

To obtain a simple construction, it is advantageous if the holding device is configured in one piece.

In particular, the holding device can be made from metal.

The extension device is preferably connectable to the stabilisation element seating without a tool and/or detachable therefrom without a tool. This makes handling of the fixation system easier for an operating surgeon.

It is advantageous if the extension device can be clamped onto the stabilisation element seating at the distal section, since this makes handling of the fixation system easier for the operating surgeon while also allowing a simpler structural form thereof.

It has proved advantageous if the distal section of the extension device engages over the stabilisation element seating in a positive-locking manner, in particular when the extension device is clamped onto the stabilisation element seating during application. This enables the extension device and the stabilisation element seating to be aligned relative to one another.

On the distal end the extension device preferably comprises at least one alignment member cooperating with the stabilisation element seating for alignment of the extension device and the anchoring element relative to one another, since this makes it easier for an operating surgeon to align the extension device and the anchoring element correctly relative to one another.

It is advantageous if the at least one alignment member is configured as a projection, which engages in particular in a positive-locking manner into an insertion opening of the stabilisation element seating for the stabilisation element, since this constitutes a structurally simple way to assure alignment.

The extension device and the stabilisation element seating are preferably aligned coaxially with one another, i.e. in use of the fixation system, axes respectively defined by the extension device and the stabilisation element seating coincide. It is thus evident for the operating surgeon by means of the extension device outside the body, which position the stabilisation element seating occupies in the interior of the body. Therefore, references to the axis of the extension device in the advantageous embodiments of the fixation system explained above should at the same time be taken as reference to the axis of the stabilisation element seating in this embodiment. Thus, if the ultrasound field of the ultrasound probe lies in the sagittal plane, for example, this sagittal plane is a plane defined by the stabilisation element seating. If the operating surgeon ensures that the stabilisation element is seen to be in the sagittal plane in the ultrasound image, he can be sure that he moves the stabilisation element in the correct insertion direction towards the stabilisation element seating. Accordingly, the transversal plane is a plane that intersects the sagittal plane defined by the stabilisation element seating at right angles. By checking that the stabilisation element intersects the transversal plane at as steep an angle as possible, ideally 90°, by means of the ultrasound image, the operating surgeon can ensure that the stabilisation element is moved in the insertion direction towards the stabilisation element seating.

In a simple structural configuration and to simplify handling of the fixation system, it is advantageous if the extension device is configured to be intrinsically symmetrical or substantially symmetrical.

It can preferably be provided that the extension device has a cylindrical or substantially cylindrical cross-section and in particular in this case has an outer contour that is configured to correspond to a contour of the coupling section of the holding device.

It has proved advantageous if the extension device forms an axially extended sleeve. If it engages over the stabilisation element seating at the distal section, the sleeve forms an access point for the operating surgeon into the interior of the body, i.e. a working cannula, by means of which a fixation element can be inserted, for example, to fix the stabilisation element on the anchoring element.

The sleeve can be configured as a telescopic sleeve. The probe coupled thereto can then be moved axially relative to the surface of the body and applied thereto. Depending on the magnitude of the ultrasound field emitted by the probe, body areas located on both sides of the sleeve can be detected with the probe.

It can be provided that the extension device is made from metal.

The extension device is preferably configured in one piece, since this allows a simple structural form of the fixation system.

It is advantageous if the anchoring element is configured as a bone screw with a shank, which can be screwed into the bone, and with a screw head forming the stabilisation element seating. A reliable anchorage of the screw on the bone or on a bone fragment can be assured by means of the shank. The screw head serves to receive the stabilisation element, which can be secured to this, for example, by means of a clamping screw. The screw head defines an axis, which is advantageously aligned coaxially with an axis defined by the extension device, as mentioned above. The extension device advantageously forms a working cannula, which engages over the screw head in particular in a positive-locking manner during application of the fixation system.

It is advantageous if the screw head is slotted and in this way forms an insertion opening for the stabilisation element. In particular, the screw head thus forms a so-called "tulip head" and the anchoring element thus forms a so-called "tulip-head screw". An alignment member arranged on the distal section of the extension device can engage into the slit in particular in a positive-locking manner in order to ensure a correct alignment of the extension device relative to the screw head.

In a particular application of the fixation system it is advantageous if the bone screw is a pedicle screw, which can be anchored to a pedicle of a vertebra. In this case, the fixation system is especially a spinal fixation system.

The bone screw can be a monoaxial screw, in which the shank is connected rigidly to the screw head and in which the shank and the screw define a common axis. This is advantageously oriented coaxially to the axis of the extension device.

However, it is also possible that the bone screw is a polyaxial screw, in which the screw head is lockably articulated to the shank. In this case, the screw head advantageously defines an axis aligned coaxially with the axis of the extension device.

The fixation system advantageously comprises at least one stabilisation element for connecting the anchoring element to a further anchoring element in order to fix bones or bone fragments to one another in a defined relative position.

It can be provided that the stabilisation element has a longitudinal extent.

To obtain a simple structure of the fixation system, it is advantageous in particular if the stabilisation element is a rod, especially a metal rod.

As already mentioned, the fixation system can be combined with already existing ultrasound probes. However, it is advantageous if the fixation system comprises an ultrasound probe that is able to be positioned in the probe seating. This provides the possibility of adapting the individual components of the fixation system, in particular the holding device and the ultrasound probe, to one another in the best possible manner.

It has proved advantageous upon application of the fixation system if the ultrasound probe is a convex probe.

The ultrasound probe preferably has a grip with a non-round cross-section. As a result, it can be handled in a simpler manner by the operating surgeon. In the case where the through opening of the holding device likewise has a non-round cross-section, the alignment of the ultrasound probe relative to the holding device is made easier for the operating surgeon.

The fixation system advantageously has two or more anchoring elements, which can be connected to one another by means of one or more stabilisation elements in order to fix bones or bone fragments to one another in a defined relative position. In particular, the fixation system can comprise two or more bone screws.

It can be provided that the fixation system comprises a plurality of extension devices, which can be configured identically. Each anchoring element can be provided with an associated separate extension device.

Moreover, it is possible that the fixation system has a plurality of holding devices, which are adapted to different ultrasound probes and are respectively configured, for example, to correspond with one of the holding devices explained above.

As mentioned above, the present invention also relates to an ultrasonic targeting device for an orthopaedic fixation system. A targeting device according to on aspect of the invention comprises a holding device, an extension device and also a coupling device for coupling the holding device to the extension device, wherein this relates to a holding device, an extension device and a coupling device of the fixation system according to the first aspect of the invention or of one of the aforementioned fixation systems. Features of the holding device, the extension device and the coupling device of the fixation system according to the first aspect of the invention or one of the aforementioned fixation systems can thus be features of the holding device, the extension device and the coupling device of the targeting device according to preferred embodiments of the invention.

The targeting device according to preferred embodiments of the invention can be detachably connected to an anchoring element by means of the extension device and an ultrasound probe can be positioned in the probe seating of the holding device of the targeting device according to preferred embodiments of the invention.

The advantages mentioned in association with the explanation of the fixation system according to the first aspect of the invention can also be achieved with a conventional fixation system using the targeting device according to preferred embodiments of the invention.

The present invention further relates to an orthopaedic fixation method. The fixation system according to the first aspect of the invention enables a fixation method to be conducted, in which the advantages mentioned in association with the explanation of the fixation system according to the first aspect the invention can be achieved.

In a second aspect of the invention, a fixation method is provided in which an orthopaedic fixation system is used including an anchoring element, which is anchored to a bone, which is connected by means of a stabilisation element to a further anchoring element. The stabilisation element is inserted into a stabilisation element seating of the anchoring element in an insertion direction. The fixation system includes an extension device for an anchoring element, which is detachably connected at a distal section to the anchoring element and projects out of the body at a proximal section. The proximal section of the extension device is coupled to a holding device for an extracorporeal ultrasound probe by means of a coupling device, and the ultrasound probe is positioned in a probe seating of the holding device and the stabilisation element is detected by means of the ultrasound probe.

In a perspective representation FIG. 1 shows a preferred embodiment of a fixation system 10 according to one aspect of the invention, this especially being a spinal fixation system for the fixation of a vertebral column, of which only two vertebral bodies 12 and 14 are shown schematically in FIG. 1. Vertebral body 14 is arranged caudally in relation to vertebral body 12.

The fixation system 10 comprises a plurality of anchoring elements, of which two anchoring elements 16 and 17 in the form of bone screws 18 and 19 are shown. The fixation system 10 additionally has two extension devices 20 and 21 in the form of access tubes 22 and 23 respectively, which are each associated with one of the bone screws 18 and 19 respectively. In addition, the fixation system 10 can comprise further anchoring elements and/or extension devices (not shown).

The fixation system 10 further comprises an elongated stabilisation element 24 in the form of a rod 25, e.g. made of metal, and also a tool 26 for handling this, which can be secured to the rod 25 at the end. In addition, the fixation system 10 can comprise further stabilisation elements (not shown).

Figure 5:
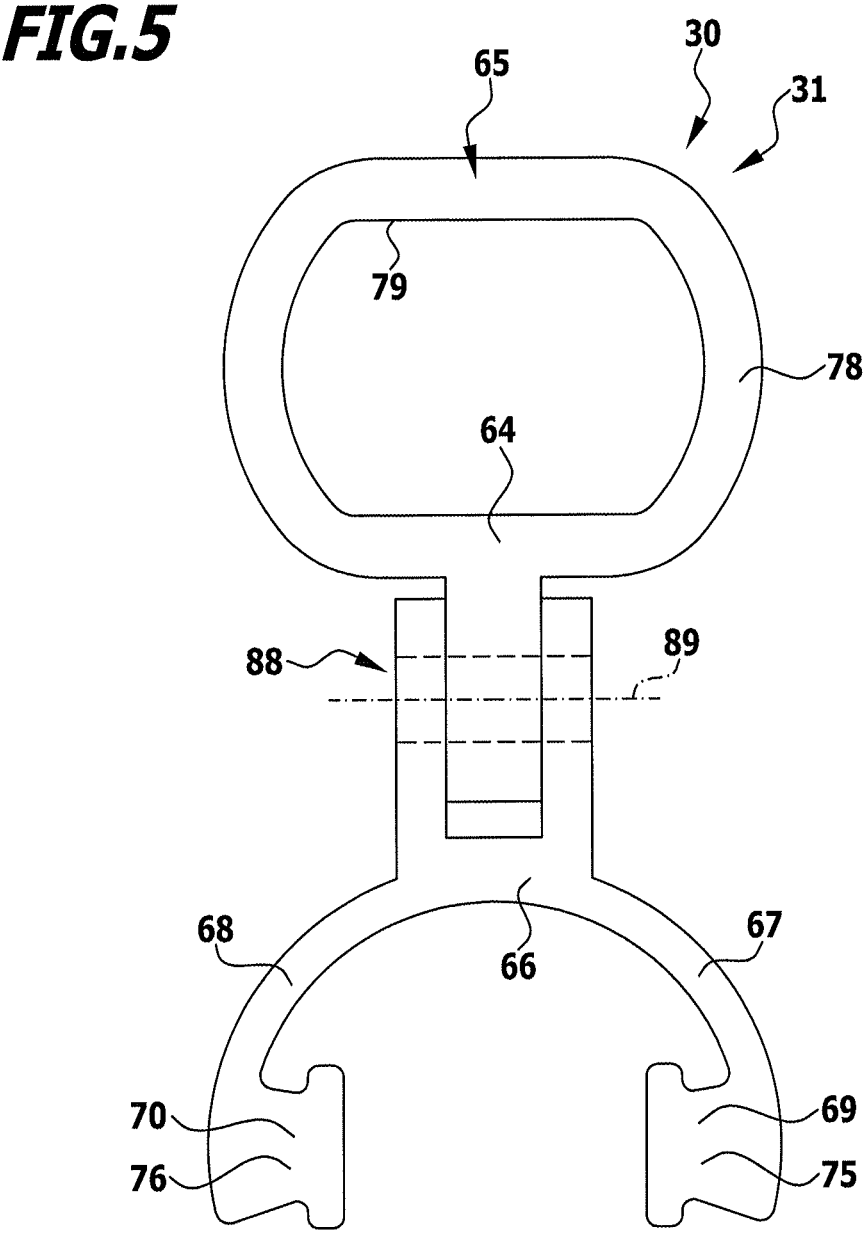
FIG. 5 is a plan view of a second holding device of the fixation system from FIG. 1.
Figure 7:
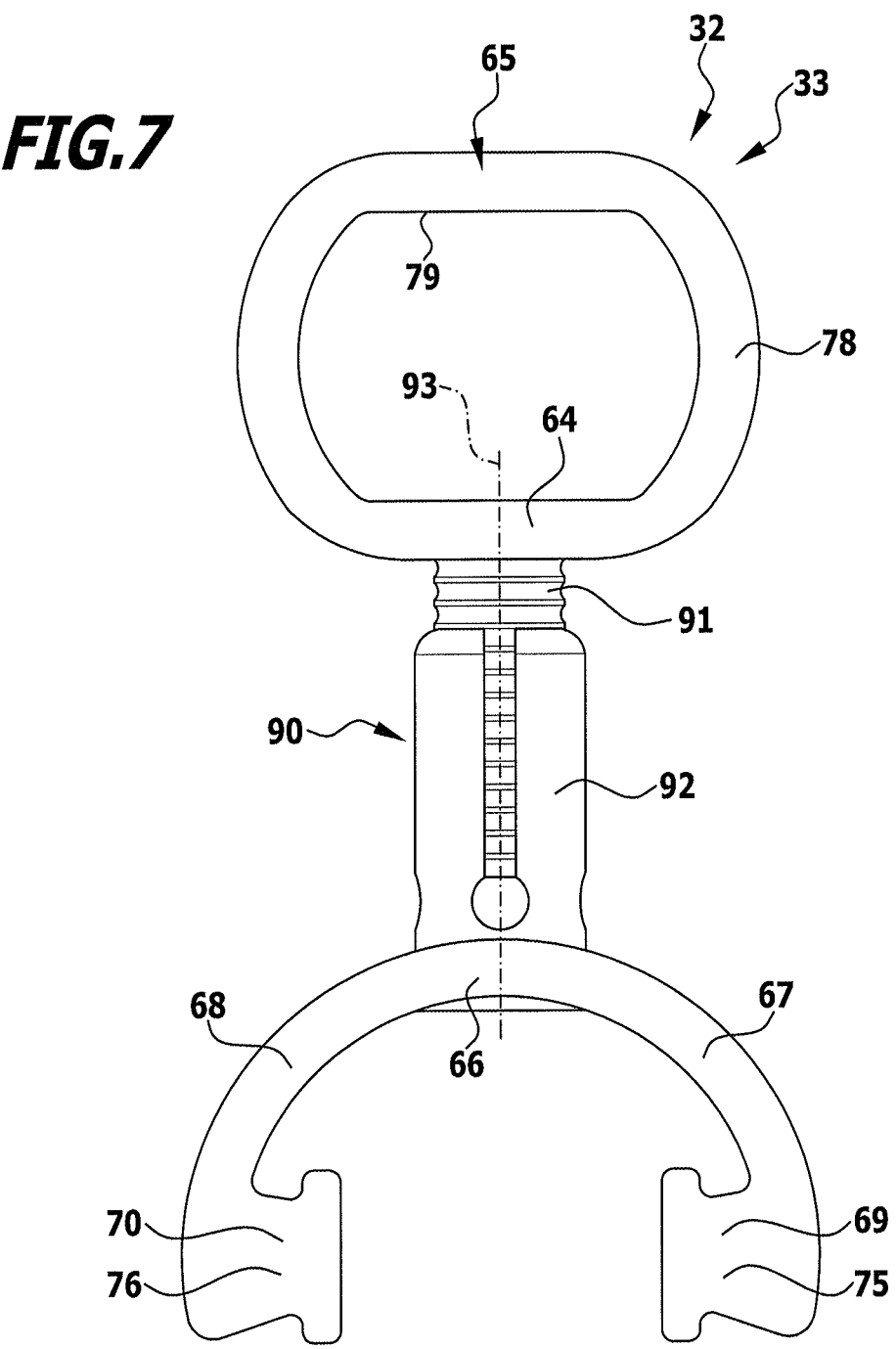
FIG. 7 is a plan view of a third holding device of the fixation system from FIG. 1.

The fixation system 10 further comprises a holding device 27, referred to hereafter as adapter 28, for an ultrasound probe 29, which is also a component of the fixation system 10. The fixation system 10 also comprises two further holding devices 30 and 32, referred to hereafter as adapters 31 and 33 respectively (FIGS. 5 and 7).

The bone screws 18 and 19 are formed identically, and therefore only bone screw 18 will be described in more detail below. The bone screw 18 is a pedicle screw for anchoring in a pedicle of the vertebral bodies 12 or 14. The bone screw 18 is a monoaxial screw with a shank 34 comprising a thread and also with a screw head 35, which is rigidly connected to the shank 34. The shank 34 and the screw head 35 define a screw axis 36.

Alternatively, the bone screws 18 or 19 can be configured as polyaxial screws, or additionally the fixation system 10 can have anchoring elements (not shown) in the form of polyaxial screws.

The screw head 35 is configured as a so-called "tulip head" 37 and comprises two longitudinal slits 38 and 39 diametrically opposed to one another in relation to the screw axis 36.

The slits 38 and 39 form insertion openings 40 and 41 respectively for the rod 25 to detachably connect this to the bone screw 18 in a known manner. This is achieved, for example, by clamping the rod 26 with the tulip head 37 by means of a clamping screw not shown in the drawing. The tulip head 37 thus forms a stabilisation element seating 42.

In order to fix the vertebral bodies 12 and 14 relative to one another, it is known to connect the bone screws 18 and 19 by means of the rod 25 and secure this to the bone screws. For this it is necessary that the rod 25 is inserted into the tulip head 37 through the insertion opening 40 in a defined direction in relation to the bone screw 18. This insertion direction is represented in the drawing by an arrow given the reference 43. To ensure that the rod 24 is guided in caudal-cranial direction in the insertion direction 43, the operating surgeon can operate the tool 26 and the access tubes 22 and 23, which are detachably connectable to the bone screws 18 and 19, as explained below, for example in order to align the bone screw 18 relative to the rod 25.

The operating surgeon has no other access possibilities, since in the present case the fixation system 10 is to be worked with in a minimally invasive manner, i.e. the tool 26 and the access tubes 22 and 23 are inserted into the interior of the body only through small incisions 44 to 46. For example, depending on the position of the vertebral bodies 12 and 14 in relation to one another, the curvature of the rod 25 and the number of anchoring elements to be used, the insertion of the rod into the tulip heads of the bone screws proves difficult for the operating surgeon without auxiliary elements assisting the alignment.

As explained below, in the fixation system 10 according to one aspect of the invention the access tubes 22 and 23, the adapters 28, 31 and 33 and also the ultrasound probe 29 are used to assist the operating surgeon.

The access tubes 22 and 23 are formed identically, and therefore only access tube 22 will be discussed below. The access tube 22 is an elongated sleeve defining a longitudinal axis 47 with a substantially cylindrical cross-section. It has a distal section 48 and a proximal section 49, wherein "proximal" and "distal" in the present case are meant in relation to the operating surgeon located outside body. Accordingly, the access tube 22 can be firstly inserted into the interior of the body at the distal section 48 and detachably connected to the tulip head 37.

The distal section 48 can be clamped onto the tulip head 37, wherein it engages over the tulip head 37 in a positive-locking manner, so that the tulip head 37 penetrates into the distal section 48. Two alignment members on the inside in the form of projections 50 and 51 on the distal section 48 can engage into the slits 38 and 39 respectively in a positive-locking manner, so that the access tube 22 can be aligned in a clearly defined manner relative to the tulip head 37 and thus in the case of the monoaxial screw 18 also relative to the shank 34. The tulip head 37 and the access tube 22 are thus aligned coaxially with one another. Recesses arranged at the distal end of the access tube 22 (only one recess 52 is visible in FIG. 2) align with the insertion openings 40 and 41, so that the rod 25 can pass through the access tube 22 at the distal end.

The access tube 22 is configured to be intrinsically symmetrical in relation to at least one plane of symmetry containing the longitudinal axis 47, which additionally contains a straight line running in the insertion direction 43 when the access tube 22 is clamped onto the bone screw 18. This plane of symmetry spanned by the insertion direction 43 and the longitudinal axis 47 is referred to hereafter as "sagittal plane S" (oriented perpendicularly to the plane of the drawing in FIG. 3). In the present case the designation follows from the bone screws 18 and 19 being screwed into the pedicles of the vertebral bodies 12 and 14 in sagittal direction, so that these can be connected to one another in caudal-cranial direction, i.e. the insertion direction 43 also runs in caudal-cranial direction. Accordingly, the insertion direction 43 and the longitudinal axis 47 span a sagittal body plane.

On the exterior, the access tube 22 has two axially extending seatings 53 and 55 in the form of longitudinal grooves 54 and 56 respectively, which respectively extend from the distal sections 48 to the proximal section 49 and are diametrically opposed to one another in relation to the longitudinal axis 47. Because of the symmetry of the access tube 22, only the longitudinal groove 54 will be discussed below.

Figure 2:
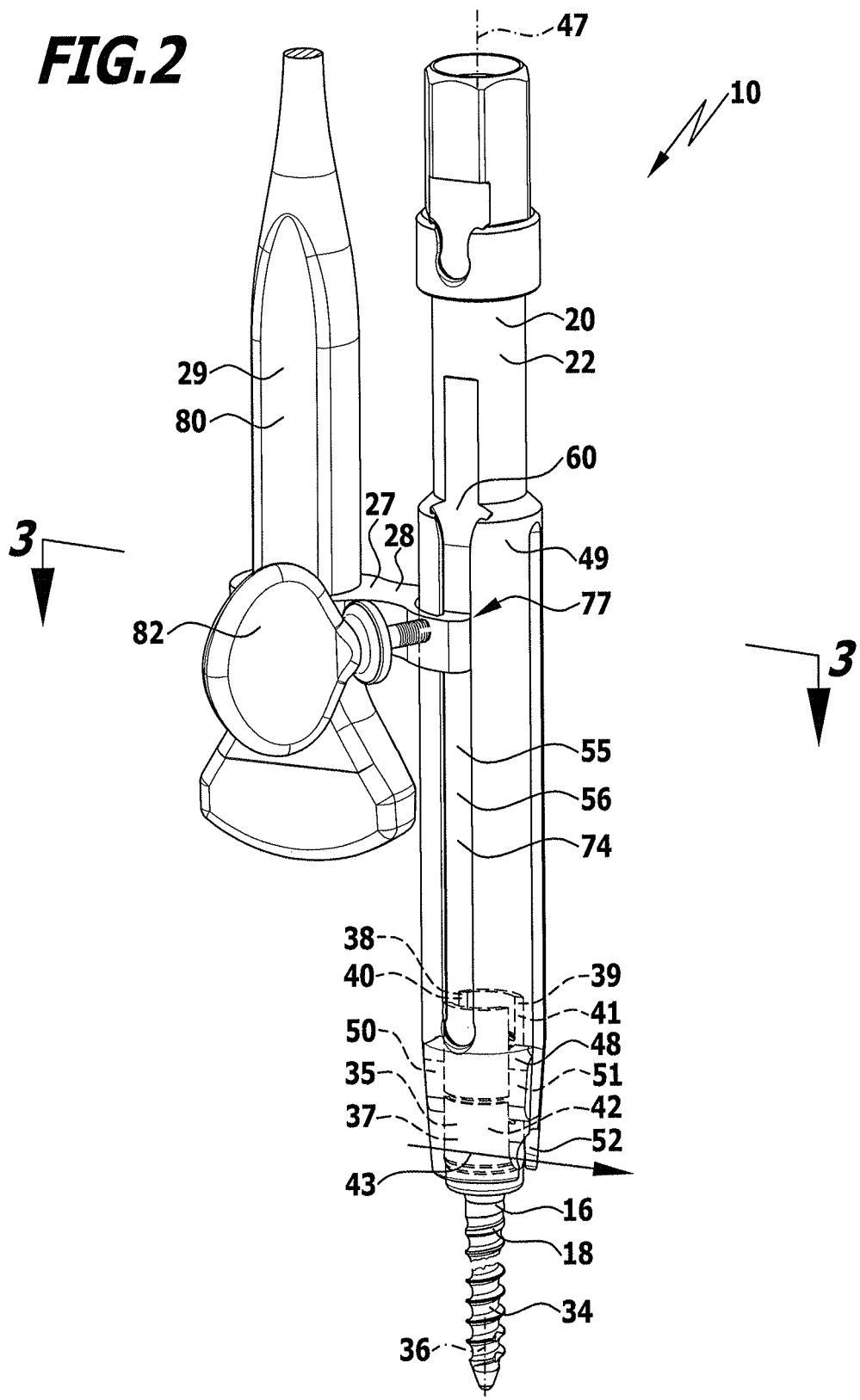
FIG. 2 is a further perspective representation of a part of the fixation system from FIG. 1.

The longitudinal groove 54 is formed in a wall 57 of the access tube 22. In radial direction from the inside outwards, it comprises a first seating region 58 and also an adjoining second seating region 59, which is narrowed in relation to the first seating region 48. At the proximal end the longitudinal groove 54 comprises an insertion opening 60 that widens in a funnel shape (FIGS. 1 and 2).

Directly adjacent to the longitudinal groove 54 the access tube 22 has an indication arrangement 61 on the outside with a scale 62 extending from the distal section 48 to the proximal section 49. By means of the scale the operating surgeon can determine how deep the distal end of the access tube 22 penetrates into the interior of the body, i.e. how great the penetration depth d of the distal end is in relation to the body surface 63. Thus, the operating surgeon can also determine at what depth the tulip head 37, in particular its insertion openings 40 and 41 for the rod 25, is located in the interior of the body.

Figure 3:
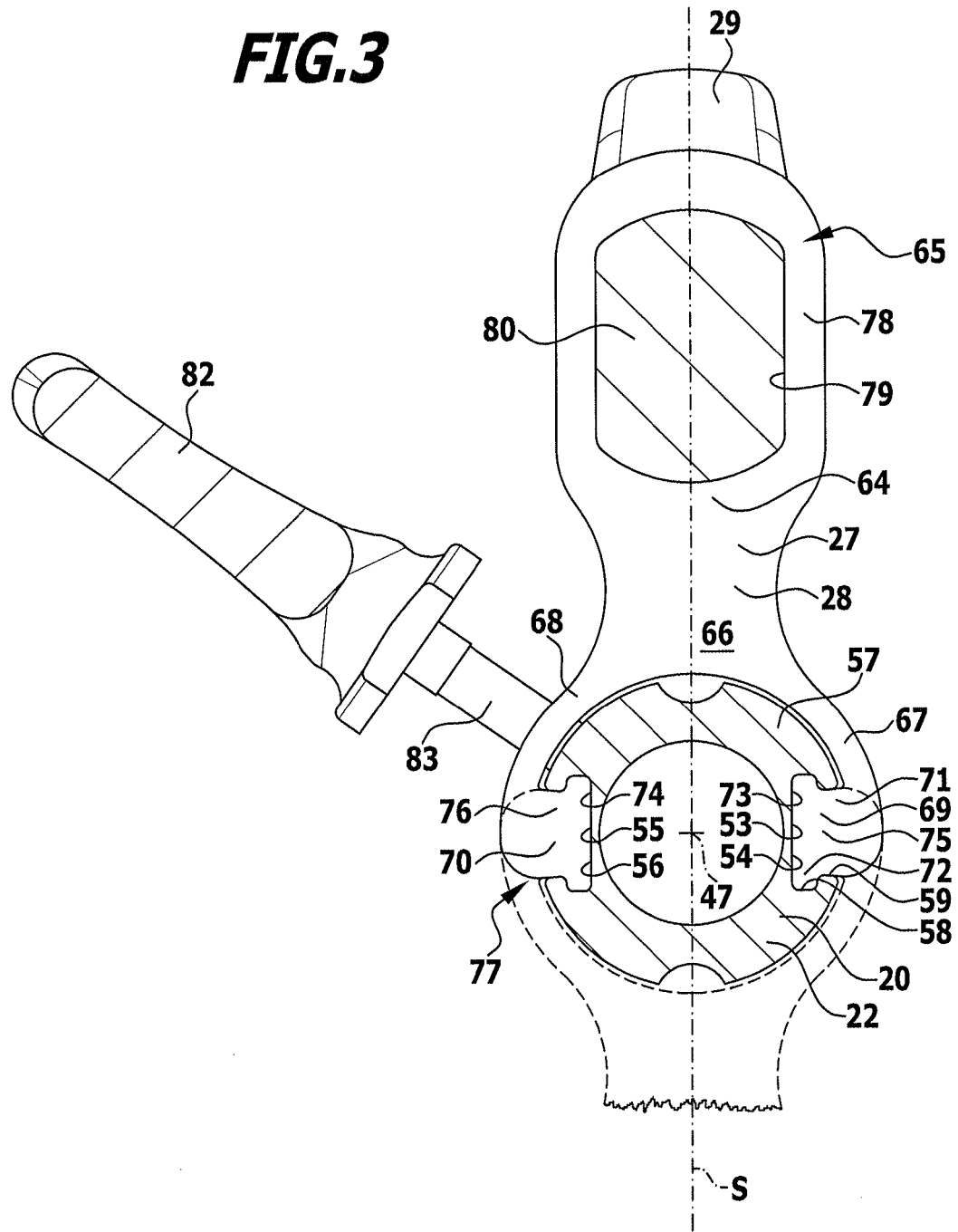
FIG. 3 is a sectional view taken along line 3-3 in FIG. 2.

As is evident in particular from FIG. 3, the already mentioned adapter 28 comprises a holding section 64 with a probe seating 65 for the ultrasound probe 29. The holding section 64 is connected to a coupling section 66 and in particular is connected in one piece. The coupling section 66 is arranged on the adapter 28 on the end side and forms a C-shaped contour with two coupling arms 67 and 68, which bear projections 69 and 70 respectively on their free ends. The contour of the coupling section 66 is adapted to the outer contour of the access tube 22, so that the adapter 28 can be coupled to the access tube 22 in a space-saving manner, as explained below.

The adapter 28 is configured to be substantially symmetrical in relation to a plane of symmetry, which coincides with the sagittal plane S on coupling the adapter 28 to the access tube 22. For this reason, the projections 69 and 70 are diametrically opposed to one another and are directed towards a centre of curvature of the coupling section 66, which lies on the longitudinal axis 47. Because of the symmetry of the adapter 28, only projection 69 will be discussed below.

Projection 69 comprises a base region 71 and a head region 72 widened in relation to the base region 71. The base region 71 and the head region 72 are respectively dimensioned such that they can cooperate with the second seating region 59 or the first seating region 58 of the longitudinal groove 54 in a positive-locking manner.

The projection 69 can be inserted through the insertion opening 60 into the longitudinal groove 54, so that it engages into this in a positive-locking manner and the projection 69 and the longitudinal groove 54 engage behind one another in a positive-locking manner in a plane oriented transversely to the longitudinal axis 47 and approximately form a "dovetail connection". In this way, the adapter 28 is reliably coupled to the access tube 22 and is secured against rotation relative to this around the longitudinal axis 47. For this reason, the longitudinal grooves 54 and 56 are also referred to as first coupling members 73 and 74, and the projections 69 and 70 are referred to as second coupling members 75 and 76, which cooperate with the coupling members 73 and 74 respectively. The coupling members 73 to 76 form a coupling device 77 of the fixation system 10.

The probe seating 65 comprises a through opening 79, which is bordered by an enclosed edging 78 and is formed as a perforation of the holding section 64. The through opening 79 has a non-round cross-section, i.e. a cross-section differing from the circular form. In the case of all the adapters 28, 31 and 33 the cross-section of the through opening 79 resembles the shape of a circle, from which two diametrically opposed segments have been separated.

In particular, the shape of the through opening 79 is adapted to the cross-sectional form of a grip area 80 of the ultrasound probe 29. The grip area 80 is likewise given a non-round cross-section. In cross-section the grip area 80 has its maximum extent in a plane that is defined by the ultrasound field 81 emitted by the ultrasound probe (FIG. 1).

As a result, the grip area 80 is insertable into the probe seating 65 only in one orientation such that it is surrounded by the mounting 78 in a positive-locking manner and can thus be secured by clamping to the holding section 64. The through opening 79 has the largest clear extent in the plane of symmetry of the adapter 28. As a result of this, when the ultrasound probe 29 is coupled to the access tube 22 by means of the adapter 28, the ultrasound field 81 emitted by the ultrasound probe 29 lies in the sagittal plane S, i.e. in the plane spanned by the insertion direction 43 and the longitudinal axis 47. This occurs "automatically" to a some extent, since the operating surgeon can insert the ultrasound probe 29 into the probe seating 65 only in one orientation.

The fixation system 10 according to one aspect of the invention can be used in the following manner to make insertion of the rod 25 into the tulip head 37 easier, wherein it is assumed that the rod 25 has already been inserted into the screw head of the bone screw 19 (FIG. 1):

The ultrasound probe 29, which can be a convex probe, for example, is inserted into the probe seating 65 and is held in the mounting 78 by clamping, for example. The adapter 28 is coupled to the access tube 22 by inserting the projections 69 and 70 into the longitudinal grooves 54 and 56 respectively. The adapter 28 can then be displaced in axial direction, i.e. along the longitudinal axis 47, relative to the access tube 22 until the ultrasound probe 29 comes into contact with the body surface 63 without any gap to allow penetration of the ultrasound field 81 into the body. The longitudinal grooves 54 and 56 guide the projections 69 and 70 respectively in this case.

The adapter 29 can then be secured to the access tube 22, in particular by clamping, by means of a fixation device 82 included by the fixation system 10. The fixation device 82 comprises a manually operable clamping screw 83 in the form of a so-called "thumb screw". The clamping screw 83 can be screwed through a thread (not shown in the drawing) in the coupling arm 68 and be supported against the access tube 22 on the outside (FIG. 3) to clamp the adapter 28 to the access tube 22.

Figure 4:
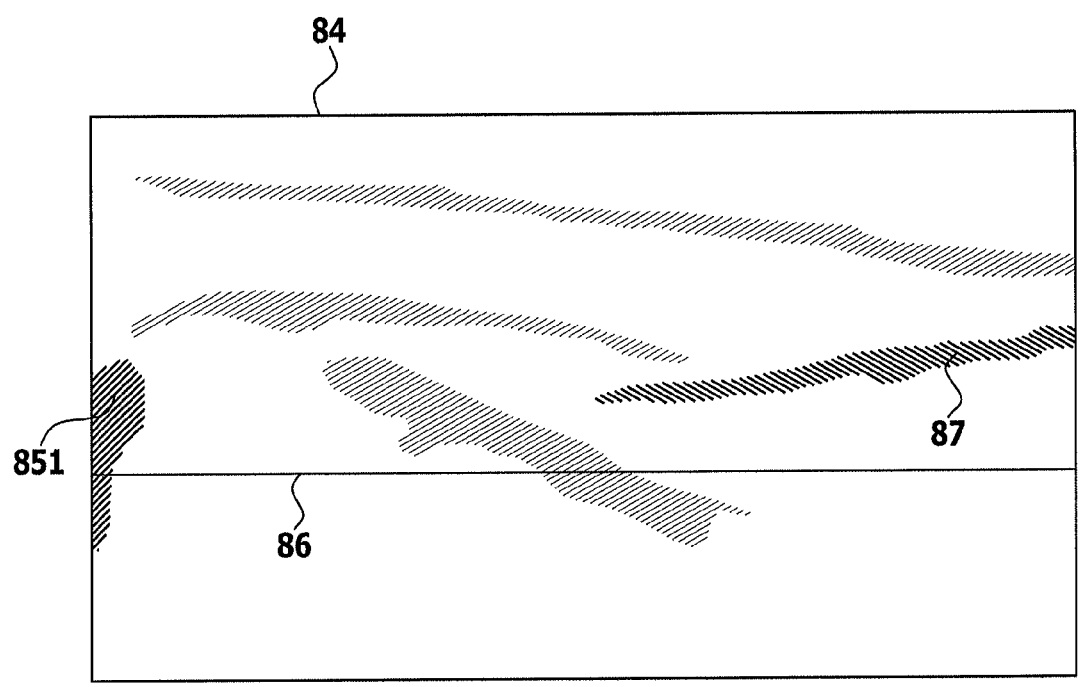
FIG. 4 is a perspective representation of an ultrasound image recorded with the ultrasound probe of the fixation system from FIG. 1.

The ultrasound probe 29 can be connected to a display unit (not shown in the drawing) in a known manner. FIG. 4 schematically shows an ultrasound image 84 detected by the ultrasound probe 29.

The ultrasound probe 29 can view a part of the sagittal plane S that lies between the bone screws 18 and 19 (FIG. 1). In this case, the ultrasound probe 29 also detects an edge region 85 of the access tube 22 and the bone screw 18 as a structure 851 in the ultrasound image 84. The edge region 85 comprises in particular slit 38, into which the rod 25 is to be inserted, since the slit 38 also lies in the sagittal plane S. To make it easier for the operating surgeon to locate the structure 851 in the ultrasound image 94, a target marking 86 can be inserted in the ultrasound image 84 with an evaluation unit, for example, at the depth at which the structure 851 is to be expected. The position of the marking 86 on the ultrasound image is determinable on the basis of the penetration depth d of the access tube 22 into the interior of the body.

Depending on how far the bone screw 19 is spaced from bone screw 18, it is possible that this or the access tube 23 attached thereto is also visible in the ultrasound image 84.

Since the rod 25 must be inserted into the tulip head 37 in the insertion direction 43 and thus in the sagittal plane S, the operating surgeon can recognise on the basis of the size of the ultrasound reflection 87 of the rod 25 in the ultrasound image 84 whether the rod 25 lies in the sagittal plane S and is being moved in the insertion direction. The larger the ultrasound reflection 87 recognisable in the ultrasound image 84, the flatter the intersection of the rod 25 with the sagittal plane S, and in the ideal case it lies completely in the sagittal plane S.

The rod 25 guided from the bone screw 19 in the direction of the bone screw 19 can thus be detected in a user-friendly manner by means of the ultrasound probe 29. Thus, by grasping the tool 26 and the access tube 22, the operating surgeon can align the rod 25 relative to the tulip head 37 in a simple manner and insert this in the insertion direction 43. If the access tube 22 is moved in so doing, this results in a movement of the sagittal plane S and thus also of the ultrasound field 81, since the ultrasound probe 29 follows the movement of the access tube 22. This makes insertion of the rod 25 into the tulip head 37 considerably easier for the operating surgeon.

If it is provided to connect the rod 25 to a further bone screw beyond the bone screws 18 and 19, in the representation according to FIG. 1 left of the bone screw 18, for example, the procedure for further positioning of the rod 25 can be as follows:

On the one hand, it is possible to connect an access tube that is configured to correspond to access tube 22, for example, to the further bone screw. The adapter 28 can be uncoupled from the access tube 22 by releasing the clamping screw 83 and guiding the projections 69 and 70 out of the longitudinal grooves 54 and 56 respectively. The adapter 28 can then also be coupled to the further access tube in the manner described above and the rod 25 can be detected by means of the ultrasound probe 29 and aligned in the direction of the screw head of the further bone screw as described above.

On the other hand, it is possible to move the adapter 28 relative to the access tube 22 from the first coupling position described above, in which the area of the body located caudally in relation to the access tube 22 is detected by means of the ultrasound probe 29, into a second coupling position. The area of the body located cranially in relation to the access tube 22 can be detected by means of the ultrasound probe 29 in the second coupling position. For this, the adapter 28 should firstly be uncoupled from the access tube 22, then rotated 180° around the longitudinal axis 47 and coupled again to the access tube 22, so that projection 69 and longitudinal groove 56 and projection 70 and longitudinal groove 54 cooperate with one another. This position of the adapter 28 is represented sectionally in broken lines in FIG. 3.

Because of the symmetries of the access tube 22 and the adapter 28 the ultrasound field 81 once again lies in the sagittal plane S. In the second coupling position there is then the possibility of detecting the rod 25 as it is moved by the operating surgeon away from the tulip head 37 by means of the tool 26. It may be possible in this case to detect the tulip head 37 of the further bone screw (not shown) in the ultrasound image 84, so that the operating surgeon can align the rod 25 directly in relation to the further bone screw, as explained above.

The further adapters 31 and 33 and their method of operation in the fixation system 10 are described below with reference to FIGS. 5 to 9. The same reference numerals have been used for features of the adapters 31 and 33 that are the same or act the same as features of the adapter 28. Only the fundamental differences of the adapters 31 and 33 from adapter 28 will be discussed below. The adapters 31 and 33 are also configured to be intrinsically substantially symmetrical in relation to the plane of symmetry, which coincides with the sagittal plane S when coupling the adapters 31 or 33 to the access tube 22.

In the case of adapters 31 and 33 the probe seating 65 is rotated 90° respectively relative to the probe seating 65 of adapter 28. Therefore, it has its largest clear extent in a direction that is oriented perpendicularly to the sagittal plane S and thus perpendicularly to the insertion direction 54 and to the longitudinal axis 47 (to be understood when adapter 31 or 33 is coupled to the access tube 22).

In the case of adapters 31 and 33 the holding section 64 and the coupling section 66 are not connected to one another in one piece. Instead, the holding section 64 and the coupling section 66 of adapter 31 form a hinge 88 so that they are able to pivot relative to one another around a pivot axis 89. When adapter 31 is coupled to the access tube 22 the pivot axis 89 is oriented perpendicularly to the sagittal plane S and thus perpendicularly to the insertion direction 43 and to the longitudinal axis 47.

In the case of adapter 33 the holding section 64 and the coupling section 66 jointly form a screw connection 90 with a screw element 91 on the holding section 64 and a nut element 92 on the coupling section 66. In this way, the holding section 64 and the coupling section 66 are linearly movable relative to one another along a straight line 93, which runs in the sagittal plane S and in particular is oriented parallel to the insertion direction 43 when the adapter 33 is coupled to the access tube 22.

Figure 6:
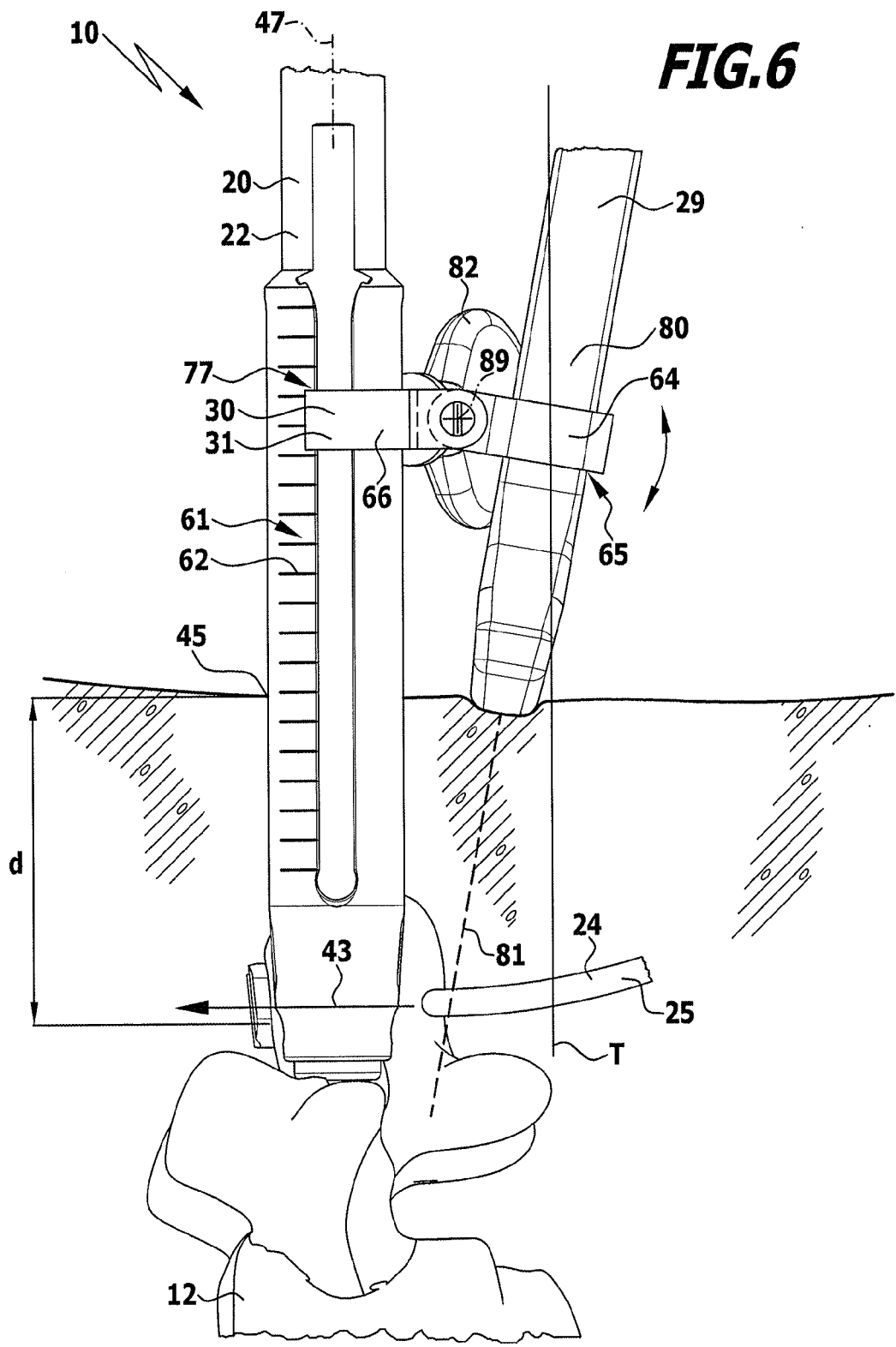
FIG. 6 is a side view of the fixation system from FIG. 1, in which the holding device from FIG. 5 is used, with the viewing direction onto a sagittal body plane.
Figure 8:
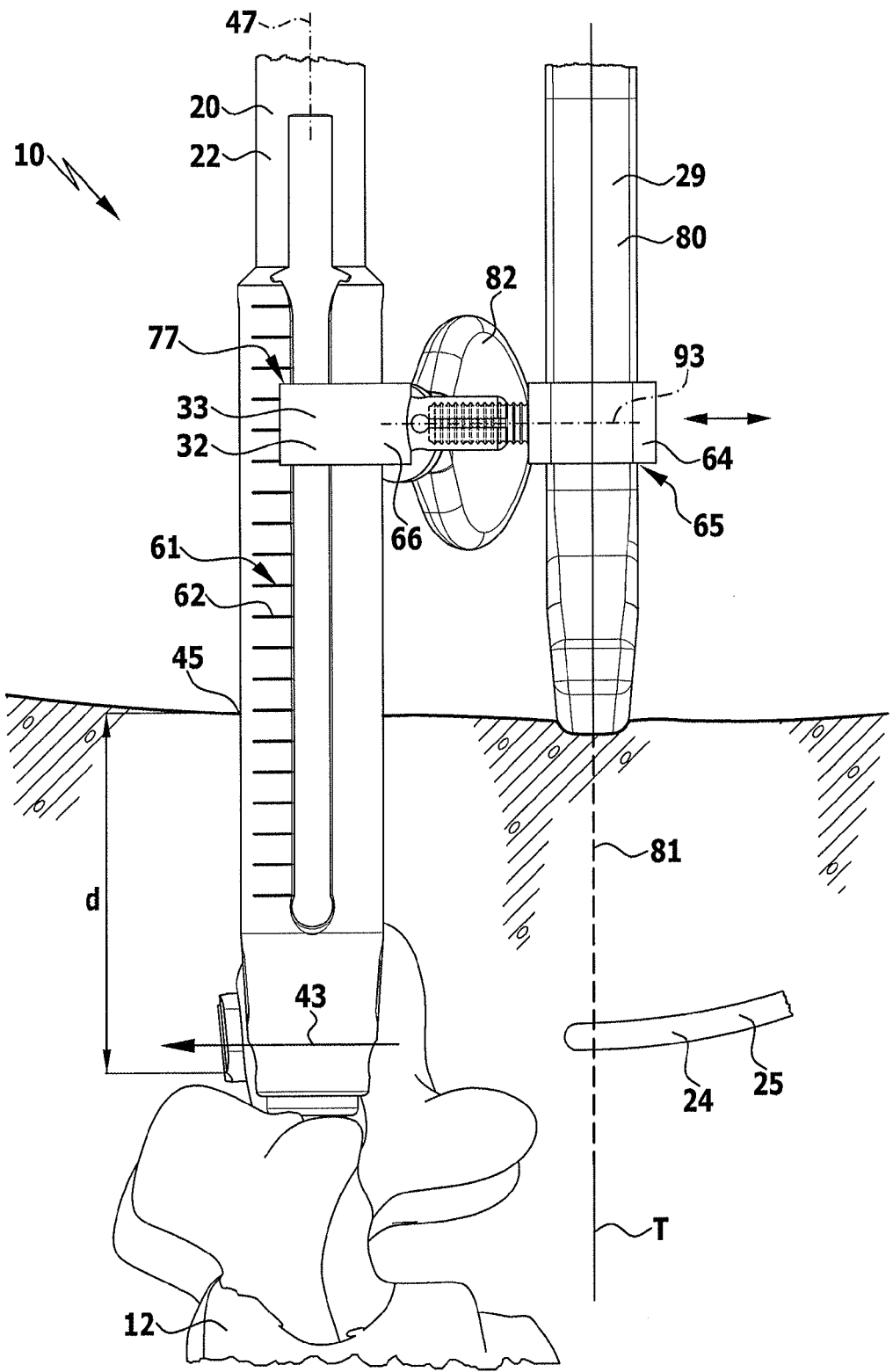
FIG. 8 is a side view of the fixation system from FIG. 1, in which the holding device from FIG. 7 is used, with the viewing direction onto a sagittal body plane.

If the ultrasound probe 29 is inserted into the probe seating of one of adapters 31 or 33 with the grip area 80 having a non-round cross-section, the ultrasound field 81 of the ultrasound probe 29 is emitted in a transversal plane T, which is oriented perpendicularly to the sagittal plane S and to which the longitudinal axis 47 runs parallel (in FIGS. 6 and 8 perpendicularly to the plane of the drawing; in the case of adapter 31 this presupposes that the holding section 64 and the coupling section 66 are arranged in a common plane). Thus, as a result of the orientation of the plane of the ultrasound field 81 in the transversal plane T, the insertion direction 43 is oriented perpendicularly to the plane of the ultrasound field 81. The centre of the ultrasound field 81 runs in the sagittal plane S.

If adapter 31 is used with the fixation system 10, the rod 25 intersecting the transversal plane T can be recognised in the ultrasound image 84 on the basis of the ultrasound reflection 87. The ultrasound reflection 87 is smaller, the steeper the angle at which the rod 25 intersects the plane of the ultrasound field 81. If the rod 25 is now guided in the direction of the tulip head 37, the operating surgeon can, for example, pivot the holding section 64 relative to the coupling section 66 around the pivot axis 89 such that the plane of the ultrasound field 81 is pivoted relative to the transversal plane T and the tip of the rod 25 is traced in the ultrasound image (FIG. 6).

A target marking 94, in the region of which the appearance of the edge region 85 is to be expected, can be inserted in the ultrasound image 84. In horizontal direction h the target marking 94 lies in the centre of the ultrasound image 84, since the centre of the ultrasound field 81 runs in the sagittal plane S. In vertical direction v the position of the target marking 94 is determinable on the basis of the penetration depth d of the access tube 22. Thus, the operating surgeon is able to align the rod 25 in the direction of the tulip head 37 in a simple manner by continuing to pivot the holding section 64 and the ultrasound probe 29 held thereon, on the one hand, and by continuing to orient the ultrasound reflection 87 in the direction of the target marking 94, on the other hand. This makes it substantially simpler for the operating surgeon to insert the rod 25 into the slit 38 in the insertion direction 43.

Figure 9:
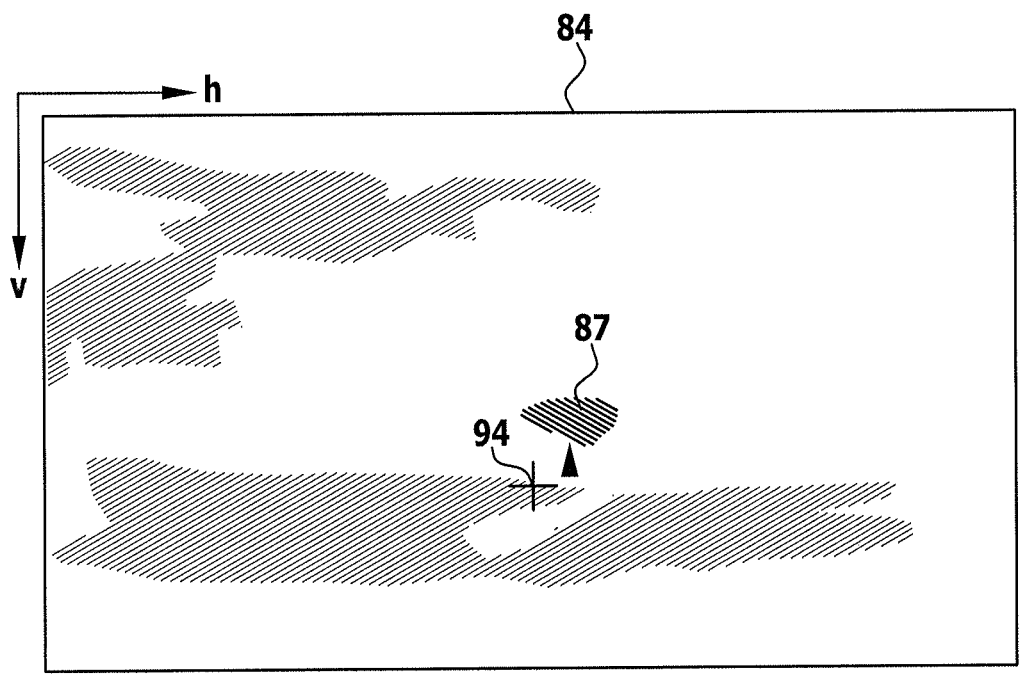
FIG. 9 is a schematic representation of an ultrasound image recorded with the ultrasound probe of the fixation system in the application represented in FIG. 6 or 8.

The operating surgeon proceeds in a similar manner when adapter 33 is used with the fixation system 10 (FIG. 8). In this case, the operating surgeon can move the holding section 64 relative to the coupling section 66 along the straight line 93 by means of the screw connection 90. This causes the transversal plane T, in which the ultrasound field 81 lies, to also move along the straight line 93. A rod 25 guided by the operating surgeon in the direction of the tulip head 37 can also be detected as ultrasound reflection 87 (FIG. 9). By continuing to move the holding section 64 relative to the coupling section 66, on the one hand, and moving the rod 25 such that the ultrasound reflection 87 is guided in the direction of the target marking 94, on the other hand, the operating surgeon can insert the rod 25 into the slit 38 of the tulip head 37 in the insertion direction 43 in a simple manner.

What is claimed:

1. An orthopaedic fixation system comprising an anchoring element which is anchorable to a bone and at least one stabilisation element for connecting the anchoring element to a further anchoring element, wherein the anchoring element comprises a stabilisation element seating, into which the at least one stabilisation element is insertable, and also with an extension device for the anchoring element having a longitudinal extent as well as a proximal section and a distal section, which distal section is detachably fixable to the anchoring element, wherein the fixation system comprises a holding device with a probe seating for an extracorporeal ultrasound probe, a coupling device for coupling the holding device to the proximal section of the extension device, an ultrasound probe which is positionable in the probe seating, and a tool for guiding the at least one stabilization element,
the holding device and the extension device configured to be movable relative to one another, the holding device further configured to be displaceable in an axial direction relative to the extension device along an axis defined by the extension device,
the coupling device comprising at least one first coupling member on the extension device, and at least one second coupling member on the holding device,
the at least one first coupling member configured as a seating that comprises an axially extending longitudinal groove, and
the at least one second coupling member configured as a projection that cooperates with the axially extending longitudinal groove of the at least one first coupling member, the projection adapted to be displaced in the axial direction to allow axial displacement of the holding device with respect to the extension device.

2. The fixation system according to claim 1, wherein the ultrasound probe is disposable in the probe seating such that an ultrasonic field emitted by the ultrasound probe lies in a plane, which is spanned by an insertion direction, in which the stabilisation element is insertable into the stabilisation element seating, and by an axis defined by the extension device.

3. The fixation system according to claim 1, wherein the ultrasound probe is disposable in the probe seating such that an ultrasonic field emitted by the ultrasound probe lies in a plane, which is oriented perpendicularly to an insertion direction, in which the stabilisation element is insertable into the stabilisation element seating, and parallel to an axis defined by the extension device.

4. The fixation system according to claim 1, wherein the holding device is detachably couplable to the extension device.

5. The fixation system according to claim 1, wherein the holding device is transferable relative to the extension device from a first coupling position into a second coupling position and vice versa, wherein in the first coupling position and in the second coupling position the probe seating is arranged on opposed sides of the extension device.

6. The fixation system according to claim 1, wherein the fixation system comprises a fixation device for fixing the holding device relative to the extension device.

7. The fixation system according to claim 1, wherein the fixation system comprises an indicating arrangement, by means of which a penetration depth of the extension device into the body is determinable.

8. The fixation system according to claim 1, wherein the holding device comprises a coupling section, which includes or forms the at least one second coupling member, and a holding section, which is connected to said coupling section and includes or forms the probe seating.

9. The fixation system according to claim 8, wherein the probe seating comprises a through opening for the ultrasound probe formed on the holding section.

10. The fixation system according to claim 9, wherein the through opening is configured as a perforation of the holding section.

11. The fixation system according to claim 8, wherein the through opening has a non-round cross-section.

12. The fixation system according to claim 8, wherein the holding section is able to pivot relative to the coupling section around a pivot axis, which is oriented perpendicularly to a plane, which is spanned by an insertion direction, in which the stabilisation element is insertable into the stabilisation element seating, and by an axis defined by the extension device.

13. The fixation system according to claim 8, wherein the holding section is configured to be linearly movable relative to the coupling section along a movement direction, which lies in a plane, which is spanned by an insertion direction, in which the stabilisation element is insertable into the stabilisation element seating, and by an axis defined by the extension device.

14. The fixation system according to claim 1, wherein the holding device is configured in one piece.

15. The fixation system according to claim 1, wherein the extension device is clampable onto the stabilisation element seating at the distal section.

16. The fixation system according to claim 1, wherein the extension device and the stabilisation element seating are aligned coaxially to one another.

17. The fixation system according to claim 1, wherein the extension device forms an axially extended sleeve.

18. The fixation system according to claim 1, wherein the anchoring element is configured as a bone screw with a shank, which is screwable into the bone, and with a screw head forming the stabilisation element seating.

19. The fixation system according to claim 18, wherein the screw head is slotted and in this way forms an insertion opening for the stabilisation element.

20. The fixation system according to claim 1, wherein the stabilisation element is a rod.

21. The fixation system according to claim 1, wherein the ultrasound probe is a convex probe.

* * * * *